(12) United States Patent
Hoffman et al.

(10) Patent No.: US 12,064,778 B2
(45) Date of Patent: Aug. 20, 2024

(54) ELECTRONIC SAFETY FEATURE FOR AN AUTOMATED AEROSOL DISPENSING DEVICE

(71) Applicant: Ecological Balancing Technologies Corporation, Wilmington, DE (US)

(72) Inventors: Michael Hoffman, Moshav Udim (IL); Pini Pinhas Gross, Yavne (IL)

(73) Assignee: Ecological Balancing Technologies Corporation, Wilmington, DE (US)

( * ) Notice: Subject to any disclaimer, the term of this patent is extended or adjusted under 35 U.S.C. 154(b) by 954 days.

(21) Appl. No.: 16/980,393

(22) PCT Filed: Mar. 12, 2019

(86) PCT No.: PCT/IB2019/052007
§ 371 (c)(1),
(2) Date: Sep. 13, 2020

(87) PCT Pub. No.: WO2019/175774
PCT Pub. Date: Sep. 19, 2019

(65) Prior Publication Data
US 2021/0046497 A1    Feb. 18, 2021

Related U.S. Application Data

(60) Provisional application No. 62/641,442, filed on Mar. 12, 2018.

(51) Int. Cl.
*B05B 1/00* (2006.01)
*A61L 2/24* (2006.01)
(Continued)

(52) U.S. Cl.
CPC .............. *B05B 12/081* (2013.01); *A61L 2/24* (2013.01); *A61L 9/14* (2013.01); *A61M 11/00* (2013.01);
(Continued)

(58) Field of Classification Search
None
See application file for complete search history.

(56) References Cited

U.S. PATENT DOCUMENTS

| 2,293,722 A | 8/1942 | Erickson |
| D221,836 S | 9/1971 | Giles et al. |
| (Continued) | | |

FOREIGN PATENT DOCUMENTS

| CN | 1177636 | 4/1998 |
| CN | 1642827 | 7/2005 |
| (Continued) | | |

OTHER PUBLICATIONS

International Preliminary Report on Patentability Dated Dec. 3, 2020 From the International Bureau of WIPO Re. Application No. PCT/IB2019/054141. (9 Pages).
(Continued)

*Primary Examiner* — Jyoti Nagpaul (57) ABSTRACT

An aerosol dispensing device includes an atomizer configured to atomize a liquid contained in a cartridge, an actuator configured to actuate activity of the atomizer, a reader configured to read data attached to the cartridge while the cartridge is installed in the device and a controller. The controller is configured to receive data from the reader, verify authenticity of the cartridge based on the data received, initiate activity of the actuator based on verifying that the cartridge is authentic, and block activity of the actuator based on verifying that the cartridge is not authentic.

29 Claims, 7 Drawing Sheets

(51) Int. Cl.
  *A61L 9/14* (2006.01)
  *A61M 11/00* (2006.01)
  *A61M 15/00* (2006.01)
  *B05B 7/24* (2006.01)
  *B05B 12/08* (2006.01)
  *B05B 12/12* (2006.01)
  *B65D 83/20* (2006.01)
  *B65D 83/26* (2006.01)

(52) U.S. Cl.
  CPC ......... *A61M 15/009* (2013.01); *B05B 7/2424* (2013.01); *B05B 12/12* (2013.01); *B65D 83/205* (2013.01); *B65D 83/262* (2013.01); *B65D 83/265* (2013.01); *A61M 2205/60* (2013.01)

(56) References Cited

U.S. PATENT DOCUMENTS

| | | |
|---|---|---|
| 3,675,832 A | 7/1972 | Ruscitti |
| D239,922 S | 5/1976 | Utley |
| D250,394 S | 11/1978 | Menius |
| 4,164,055 A | 8/1979 | Townsend |
| 4,245,788 A | 1/1981 | Wright |
| D279,452 S | 7/1985 | Beechuk |
| D284,362 S | 6/1986 | Biesecker |
| D309,711 S | 8/1990 | Biesecker |
| D376,760 S | 12/1996 | Sykes |
| D433,336 S | 11/2000 | Weber |
| 6,405,944 B1 | 6/2002 | Benalikhoudja |
| D472,471 S | 4/2003 | McClure et al. |
| D473,143 S | 4/2003 | McClure et al. |
| D489,992 S | 5/2004 | Brauner et al. |
| D571,662 S | 6/2008 | Clark et al. |
| 7,858,336 B1 | 12/2010 | Garner et al. |
| D630,946 S | 1/2011 | Crawford |
| D656,599 S | 3/2012 | Browder |
| D663,215 S | 7/2012 | Clay et al. |
| D667,101 S | 9/2012 | Browder |
| D673,253 S | 12/2012 | Mack |
| D678,496 S | 3/2013 | Browder |
| 8,986,610 B2 | 3/2015 | Ben Haim |
| 9,486,552 B1 | 11/2016 | Ansley et al. |
| 9,573,750 B2 | 2/2017 | Seling et al. |
| D805,909 S | 12/2017 | Matsuishi |
| D875,532 S | 2/2020 | Lehanneur |
| D879,613 S | 3/2020 | Lehanneur |
| 10,814,028 B2 * | 10/2020 | Becker ................. A61L 9/127 |
| 2002/0042965 A1 | 4/2002 | Salem et al. |
| 2003/0189066 A1 | 10/2003 | Schiller |
| 2004/0221415 A1 | 11/2004 | Tondra et al. |
| 2005/0160553 A1 | 7/2005 | Gregory |
| 2005/0252930 A1 | 11/2005 | Contadini et al. |
| 2007/0217945 A1 | 9/2007 | Selander |
| 2008/0216273 A1 | 9/2008 | Medema et al. |
| 2009/0238716 A1 | 9/2009 | Weening |
| 2009/0265876 A1 | 10/2009 | Gardner et al. |
| 2009/0324815 A1 | 12/2009 | Nielsen et al. |
| 2010/0021576 A1 | 1/2010 | Chang et al. |
| 2011/0214245 A1 | 9/2011 | Bassett |
| 2012/0152882 A1 | 6/2012 | Tune |
| 2012/0168971 A1 | 7/2012 | Hansen et al. |
| 2013/0015956 A1 | 1/2013 | Wegelin et al. |
| 2013/0068783 A1 | 3/2013 | Gasper et al. |
| 2014/0007866 A1 | 1/2014 | Yuki et al. |
| 2014/0263426 A1 | 9/2014 | Gasper |
| 2016/0073844 A1 | 3/2016 | Park |
| 2016/0101925 A1 | 4/2016 | Franz et al. |
| 2016/0183538 A1 | 6/2016 | Taghavi et al. |
| 2016/0325055 A1 | 11/2016 | Cameron |
| 2017/0000305 A1 | 1/2017 | Gordon et al. |
| 2017/0035262 A1 | 2/2017 | Li et al. |
| 2017/0035925 A1 | 2/2017 | Sevy |
| 2017/0348364 A1 | 12/2017 | Garner et al. |
| 2018/0368312 A1 | 12/2018 | Strang |
| 2020/0405781 A1 | 12/2020 | Holzapfel et al. |
| 2020/0407807 A1 | 12/2020 | Holzapfel et al. |
| 2020/0407808 A1 | 12/2020 | Holzapfel et al. |
| 2020/0407809 A1 | 12/2020 | Holzapfel et al. |
| 2021/0046256 A1 | 2/2021 | Hoffman et al. |
| 2021/0204774 A1 | 7/2021 | Dery et al. |

FOREIGN PATENT DOCUMENTS

| | | |
|---|---|---|
| CN | 1934241 | 3/2007 |
| CN | 103589655 | 2/2014 |
| CN | 103703121 | 4/2014 |
| CN | 104487566 | 4/2015 |
| CN | 104688895 | 6/2015 |
| CN | 104736162 | 6/2015 |
| CN | 204501790 | 7/2015 |
| CN | 303340433 S | 8/2015 |
| CN | 105087423 | 11/2015 |
| CN | 105219669 | 1/2016 |
| CN | 205032305 | 2/2016 |
| CN | 107567493 | 1/2018 |
| CN | 107723267 | 2/2018 |
| KR | 20-2009-0007893 | 8/2009 |
| KR | 10-2014-0128870 | 11/2014 |
| KR | 10-2017-0130341 | 11/2017 |
| WO | WO 01/34182 | 5/2001 |
| WO | WO 2016/060934 | 4/2016 |
| WO | WO 2016/118850 | 7/2016 |
| WO | WO 2016/118864 | 7/2016 |
| WO | WO 2019/175774 | 9/2019 |
| WO | WO 2019/175775 | 9/2019 |
| WO | WO 2019/175777 | 9/2019 |
| WO | WO 2019/175777 A8 | 9/2019 |
| WO | WO 2019/175780 | 9/2019 |
| WO | WO 2019/175782 | 9/2019 |
| WO | WO 2019/175782 A8 | 9/2019 |
| WO | WO 2019/175783 | 9/2019 |
| WO | WO 2019/224691 | 11/2019 |
| WO | WO 2019/175783 A8 | 10/2020 |

OTHER PUBLICATIONS

Restriction Official Action Dated Jul. 13, 2021 from the US Patent and Trademark Office Re. U.S. Appl. No. 17/019,568. (5 pages).
Restriction Official Action Dated Jul. 7, 2021 from the US Patent and Trademark Office Re. U.S. Appl. No. 17/019,280. (5 pages).
Restriction Official Action Dated Jul. 7, 2021 from the US Patent and Trademark Office Re. U.S. Appl. No. 17/019,281. (5 pages).
Notice of Allowance Dated Oct. 26, 2022 from US Patent and Trademark Office Re. U.S. Appl. No. 17/019,596. (9 pages).
Notice of Allowance Dated Mar. 9, 2022 together with Interview SUmmary Dated Feb. 16, 2022 from US Patent and Trademark Office Re. U.S. Appl. No. 16/645,509. (6 pages).
Notice of Allowance Dated Mar. 24, 2022 from US Patent and Trademark Office Re. U.S. Appl. No. 17/019,280. (4 pages).
International Preliminary Report on Patentability Dated Sep. 24, 2020 From the International Bureau of WIPO Re. Application No. PCT/IB2019/052007. (6 Pages).
Examination Report Dated Sep. 7, 2018 From the Government of India, Patent Office, Intellectual Property Building Re.: Application No. 309690.
Examination Report Dated Sep. 11, 2018 From the Government of India, Patent Office, Intellectual Property Building Re.: Application No. 309744.
International Preliminary Report on Patentability Dated Sep. 24, 2020 From the International Bureau of WIPO Re. Application No. PCT/IB2019/052016. (7 Pages).
International Preliminary Report on Patentability Dated Sep. 24, 2020 From the International Bureau of WIPO Re. Application No. PCT/IB2019/052008. (6 Pages).
International Preliminary Report on Patentability Dated Sep. 24, 2020 From the International Bureau of WIPO Re. Application No. PCT/IB2019/052010. (7 Pages).
International Preliminary Report on Patentability Dated Sep. 24, 2020 From the International Bureau of WIPO Re. Application No. PCT/IB2019/052014. (7 Pages).

(56) References Cited

OTHER PUBLICATIONS

International Preliminary Report on Patentability Dated Sep. 24, 2020 From the International Bureau of WIPO Re. Application No. PCT/IB2019/052017. (7 Pages).
International Search Report and the Written Opinion Dated Jul. 3, 2019 From the International Searching Authority Re. Application No. PCT/IB2019/052014. (16 Pages).
International Search Report and the Written Opinion Dated Jul. 3, 2019 From the International Searching Authority Re. Application No. PCT/IB2019/052017. (14 Pages).
International Search Report and the Written Opinion Dated Sep. 17, 2019 From the International Searching Authority Re. Application No. PCT/IB2019/054141. (11 Pages).
International Search Report and the Written Opinion Dated Jun. 26, 2019 From the International Searching Authority Re. Application No. PCT/IB2019/052016. (15 Pages).
International Search Report and the Written Opinion Dated Jun. 27, 2019 From the International Searching Authority Re. Application No. PCT/IB2019/052007. (12 Pages).
International Search Report and the Written Opinion Dated Jun. 27, 2019 From the International Searching Authority Re. Application No. PCT/IB2019/052008. (10 Pages).
International Search Report and the Written Opinion Dated Jun. 27, 2019 From the International Searching Authority Re. Application No. PCT/IB2019/052010. (17 Pages).
Notice of Amendment Dated Dec. 11, 2018 From the State Intellectual Property Office of the People's Republic of China Re. Application No. 201830508569.8. (2 pages).
Notification of Reason for Rejection Dated Jan. 30, 2019 From the Japanese Patent Office Re. Application No. 2018-019747. (2 Pages).
Official Action Dated Jun. 12, 2020 from the US Patent and Trademark Office Re. U.S. Appl. No. 29/640,027. (19 pages).
Official Action Dated Jun. 12, 2020 from the US Patent and Trademark Office Re. U.S. Appl. No. 29/640,032. (13 pages).
Official Action Dated Jun. 25, 2020 from the US Patent and Trademark Office Re. U.S. Appl. No. 29/653,164. (9 pages).
Cho "Characterization of Potential Probiotics Bacillus Subtilis CS90 From Soybean Paste (Doenjang) and Its Antimicrobial Activity Against Food-Borne Pathogens", Journal of Applied Biological Chemistry, 51(5): 285-291, 2008.
Gu et al. "The Preventive Effect and Therapeutic Effect of Spraying Agent of Bacillus Pab02 on Respiratory Infection in Broilers", Proceedings of the 10th in the 4th National Academic Seminar and Animal Micro-Ecology Enterprise Development Forum, p. 450-458, Aug. 1, 2010.
Jeon et al. "Screening and Characterization of Potential Bacillus Starter Cultures for Fermenting Low-Salt Soybean Past (Doenjang)", Journal of Microbiology and Biotechnology, 26(4): 666-674, Apr. 2016.
Ji et al. "Probiotic Bacillus Amyloliquefaciens SC06 Prevents Bacterial Translocation in Weaned Mice", Indian Journal of Microbiology, 53(3): 323-328, Published Online Mar. 16, 2013.
Wong et al. "An Antifungal Protein From Bacillus Amyloliquefaciens", Journal of Applied Microbiology, 105(6): 1888-1898, Dec. 2008.
Xie et al. "Isolation and Characterization of A Bacteriocin Produced by an Isolated Bacillus Subtilis LFB112 That Exhibits Antimicrobial Activity Against Domestic Animal Pathogens", African Journal of Biotechnology, 8(20): 5611-5619, Oct. 19, 2009.
Notice of Allowance Dated Mar. 4, 2022 From the US Patent and Trademark Office Re. U.S. Appl. No. 17/019,280. (7 Pages).
Restriction Official Action Dated Mar. 4, 2022 From the US Patent and Trademark Office Re. U.S. Appl. No. 17/019,596. (10 Pages).
Notice of Allowability Dated Apr. 20, 2022 from US Patent and Trademark Office Re. U.S. Appl. No. 17/019,568. (4 pages).
Official Action Dated Sep. 22, 2021 from the US Patent and Trademark Office Re. U.S. Appl. No. 17/019,280. (26 pages).
Official Action Dated Sep. 7, 2023 from the US Patent and Trademark Office Re. U.S. Appl. No. 17/057,727. (53 pages).
Official Action Dated May 26, 2022 from US Patent and Trademark Office Re. U.S. Appl. No. 17/019,596. (46 pages).
Notice of Allowance Dated Feb. 16, 2022 From the US Patent and Trademark Office Re. U.S. Appl. No. 17/019,281. (7 Pages).
Restriction Official Action Dated Sep. 20, 2023 from the US Patent and Trademark Office Re. U.S. Appl. No. 16/980,394. (11 pages).
Official Action Dated Dec. 21, 2023 from the US Patent and Trademark Office Re. U.S. Appl. No. 16/980,394. (44 pages).
Notice of Allowance Dated Feb. 14, 2024 together with Interview Summary Dated Jan. 31, 2024 from the US Patent and Trademark Office Re. U.S. Appl. No. 17/057,727. (15 pages).

* cited by examiner

ELECTRONIC SAFETY FEATURE FOR AN AUTOMATED AEROSOL DISPENSING DEVICE

RELATED APPLICATION/S

This application is a National Phase of PCT Patent Application No. PCT/IB2019/052007 having International filing date of Mar. 12, 2019, which claims the benefit of priority under 35 USC § 119(e) of U.S. Provisional Patent Application No. 62/641,442 filed on Mar. 12, 2018, The contents of the above applications are all incorporated by reference as if fully set forth herein in their entirety.

PCT Patent Application No. PCT/IB2019/052007 filed on Mar. 12, 2019 is also related to U.S. Provisional Patent Application Nos. 62/641,441, 62/641,443, 62/641,444, 62/641,445, 62/641,464. The contents of the above applications are all incorporated by reference as if fully set forth herein in their entirety.

PCT Patent Application No. PCT/IB2019/052007 filed on Mar. 12, 2019 is also related to co-filed PCT Patent Applications Nos. PCT/IB2019/052008, PCT/IB2019/052010, PCT/IB2019/052017, PCT/IB2019/052014, PCT/IB2019/052016 entitled "CARTRIDGE FOR AN AUTOMATED AEROSOL DISPENSING DEVICE, COMPOSITIONS COMPRISING BACTERIAL STRAINS AND USE THEREOF IN CONTROLLING PATHOGENIC MICROORGANISMS, COMPOSITIONS COMPRISING BACTERIAL STRAINS AND USE THEREOF IN CONTROLLING PATHOGENIC MICROORGANISMS, COMPOSITIONS COMPRISING BACTERIAL STRAINS AND USE THEREOF IN CONTROLLING PATHOGENIC MICROORGANISMS, COMPOSITIONS COMPRISING BACTERIAL STRAINS AND USE THEREOF IN CONTROLLING PATHOGENIC MICROORGANISMS", the contents of which are all incorporated by reference as if fully set forth herein in their entirety.

FIELD AND BACKGROUND OF THE INVENTION

The present invention, in some embodiments thereof, relates to an automated aerosol dispensing device and, more particularly, but not exclusively, to an automated aerosol dispensing device configured for dispensing biological material.

There are numerous devices known to atomize a liquid and deliver the atomized liquid into the surrounding air. Many of these devices are used to scent, purify, or humidify air in an enclosed room. Others of these devices are used to disinfect and deodorize. The atomized liquid may improve conditions in an indoor environment.

U.S. Pat. No. 8,986,610 entitled "Apparatus and method for dispersing liquid in aerosol," the contents of which is incorporated by reference herein, describes a system and method to deliver an atomized solution to the interior volume of a building or room utilizing a Venturi effect for the atomization. It is described that the solution may contain at least one active material including at least one of a medicament, probiotic, nutraceutical, or combinations thereof. The system includes a solution chamber; a Venturi configuration operatively associated with said solution chamber; an air inlet associated with a pressurized air inlet source; an actuator and a sensor. The solution chamber may be in the form of a replaceable cartridge.

SUMMARY OF THE INVENTION

According to some aspects of the present invention, there is provided an automated aerosol dispensing device that is equipped with a safety system to verify authenticity and monitor safe usage of a cartridge including the material to be atomized. According to some example embodiments, the safety system is configured to verify identity of a cartridge in the dispensing device and only approve activating the dispensing (e.g. the dispersion) once the cartridge has been authenticated by the safety system. In some example embodiments, the safety system is also configured to reject (not allow usage of) a cartridge that has been previously installed and possibly refilled with unknown contents. In some example embodiments, the safety system additionally provides ongoing monitoring of an expiration date of the cartridge and may stop atomization of its contents once the expiration date has been exceeded.

According to some aspects of the present invention, the automated aerosol dispensing device with the safety system includes a regulator in communication with one or more sensors that sense conditions in the surrounding environment. In some example embodiments, the regulator is configured to adjust a frequency or quantity of material that is dispensed based on input received from the one or more sensors. The adjustment may be performed automatically without user intervention.

According to an aspect of some example embodiments, there is provided an aerosol dispensing device comprising: an atomizer configured to atomize a liquid contained in a cartridge; an actuator configured to actuate activity of the atomizer; a reader configured to read data attached to the cartridge while the cartridge is installed in the device; and a controller configured to: receive data from the reader; verify authenticity of the cartridge based on the data received; initiate activity of the actuator based on verifying that the cartridge is authentic; and block activity of the actuator based on verifying that the cartridge is not authentic.

Optionally, the controller is configured to compare the data from the reader with reference data stored in memory and to verify authenticity based on the comparison.

Optionally, the memory is in a cloud and wherein the controller is configured to receive the reference data based on wireless communication.

Optionally, the memory is in a remote server that is configured to monitor operation of a plurality of aerosol dispensing devices.

Optionally, the data from the reader includes an expiration date and wherein verifying compatibility of the cartridge includes verifying that the expatriation date has not been reached.

Optionally, the data from the reader includes one or more of: state of a seal on the cartridge, identification data, part number of the product, batch number, production date, expiration date, quantity of material in the cartridge, contents of the cartridge and operating instructions.

Optionally, the device includes a first sensor configured to sense installation of the cartridge in the device and wherein the controller is configured to initiate reading the data attached to the cartridge based on the controller identifying that the cartridge has been installed.

Optionally, the device includes a second sensor configured to sense a second parameter, wherein the second parameter is related to an indoor environment surrounding the device and wherein the controller is configured to adjust at least one of frequency and duration that the actuator is activated based on output from the second sensor.

Optionally, the second parameter is humidity or level of air pollution.

Optionally, the device includes a third sensor configured to sense a third parameter, wherein the third parameter is related to the liquid.

Optionally, the controller is configured to adjust at least one of frequency and duration of the actuation based on output from the third sensor.

Optionally, the third parameter is a level of the liquid.

Optionally, the data attached to the cartridge is in the form of an active electronic tag and wherein the reader is configured alter data stored in the active electronic tag.

Optionally, the device includes a user interface and wherein the controller is configured to provide an alert on the user interface based on verifying that the cartridge is not authentic.

Optionally, the controller is configured to provide an alert to a remote server based on verifying that the cartridge is not authentic.

Optionally, the controller is configured to monitor ongoing use of the cartridge and to block activity of the actuator based on determining a change in safety of the cartridge.

Optionally, the change is due to one or more of detecting that an expiration date of the cartridge has passed and the liquid in the cartridge has been emptied.

Optionally, the controller is configured to receive input from an HVAC system and to coordinate activity of the actuator based on the input received from the HVAC.

According to an aspect of some example embodiments, there is provided a method for selectively altering microorganism balance in an indoor environment comprising: providing an aerosol dispensing device comprising: an atomizer configured to atomize a liquid contained in a cartridge; an actuator configured to actuate activity of the atomizer; and a reader configured to read data attached to the cartridge while the cartridge is installed in the device; receiving data from the reader; verifying authenticity of the cartridge based on the data received; initiating activity of the actuator based on verifying that the cartridge is authentic; and blocking activity of the actuator based on verifying that the cartridge is not authentic.

Optionally, the method includes comparing the data from the reader with reference data stored in memory; wherein the verifying is also based on the comparing.

Optionally, the memory is in a cloud and wherein the reference data is received based on wireless communication.

Optionally, the data from the reader includes an expiration date and wherein the verifying includes detecting that the expatriation date has not been reached.

Optionally, the data from the reader includes one or more of: state of a seal on the cartridge, identification data, part number of the product, batch number, production date, expiration date, quantity of material in the cartridge, contents of the cartridge and operating instructions.

Optionally, the method includes sensing installation of the cartridge with a first sensor in the device and initiating reading the data attached to the cartridge based on identifying that the cartridge has been installed.

Optionally, the method includes sensing a second parameter of an indoor environment surrounding the device and adjusting at least one of frequency and duration that the actuator is activated based on the second parameter.

Optionally, the second parameter is humidity or level of air pollution.

Optionally, the method includes sensing a third parameter related to the liquid.

Optionally, the method includes adjusting at least one of frequency and duration of activity of the actuator based on the third parameter.

Optionally, the third parameter is a level of the liquid in the cartridge.

Optionally, the data attached to the cartridge is in the form of an active electronic tag and wherein the reader is configured alter data stored in the active electronic tag. Optionally, the method includes providing an alert to one or more of a user interface of the device and a remote server based on verifying that the cartridge is not authentic.

Optionally, the method includes monitoring ongoing use of the cartridge and blocking activity of the actuator based on determining a change in safety of the cartridge.

Optionally, detecting the change includes one or more of detecting that an expiration date of the cartridge has passed and the liquid in the cartridge has been emptied.

Optionally, the method includes receiving input from an HVAC system and coordinating activity of the actuator based on the input received from the HVAC.

According to an aspect of some example embodiments, there is provided an aerosol dispensing device comprising: an atomizer configured to atomize a liquid contained in a cartridge; an actuator configured to actuate activity of the atomizer at a defined frequency and for a defined duration, wherein the actuation is performed automatically without human intervention; a controller configured to: to receive input from a first sensor configured to sense a parameter related to an indoor environment around the aerosol dispending device; and to adjust at least one of the defined frequency and the defined duration based on the input received, wherein the adjusting is performed automatically without human intervention.

Optionally, the first sensor is selected from a group including: a temperature sensor, a humidity sensor, and an air quality probe.

Optionally, the controller is configured to receive the input from the first sensor via a wireless communication channel.

Optionally, the first sensor is included in the device.

Optionally, the device includes a second sensor configured for sensing a parameter related to the liquid.

According to an aspect of some example embodiments, there is provided a method for selectively altering microorganism balance in an indoor environment comprising: providing an aerosol dispensing device comprising: an atomizer configured to atomize a liquid contained in a cartridge; an actuator configured to actuate activity of the atomizer at a defined frequency and for a defined duration, wherein the actuation is performed automatically without human intervention; actuating activity of the atomizer at a defined frequency and for a defined duration; receiving input from a first sensor configured to sense a parameter related to an indoor environment around the aerosol dispending device; and adjusting at least one of the defined frequency and the defined duration based on the input received, wherein the adjusting is performed automatically without human intervention.

Optionally, the first sensor is selected from a group including: a temperature sensor, a humidity sensor and an air quality probe.

Optionally, the input from the first sensor is received via a wireless communication channel.

Optionally, the method includes a second sensor configured for sensing a parameter related to the liquid.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention, in some embodiments thereof, relates to an automated aerosol dispensing device and, more particularly, but not exclusively, to an automated aerosol dispensing device configured for dispensing biological material.

Safety is a major concern when dealing with biological material, e.g. live organism or other active ingredients and even more so when this material is being dispensed in an indoor environment. Unregulated and unprotected operation of the aerosol dispensing device may lead to a health hazard. Although dispensing of probiotics or other bacteria suitable for being dispersed in an indoor environment to consume allergens and other irritants in an indoor environment is known to be safe, a health hazard may occur when the aerosol dispensing device is used to dispense other material that may not be safe or may be contaminated. Discerning counterfeit material, contamination of the material or malicious tampering of cartridges containing the material poses a challenge due to the nature of the material that may typically be dispersed and the operation of the dispensing device.

In known automated aerosol dispensing devices, the live organism or active material is typically in the form of a water based solution stored in a replaceable cartridge. The water based solution may be odorless and may not be readily distinguishable from water. A user attempting to install a new cartridge in the dispensing device may not be able to discern a condition of the contents based on visual inspection or odor. Furthermore, atomization of the solution with the automated aerosol dispensing device may typically go unnoticed by occupants of the indoor environment. If contents of the dispensed solution are faulty, occupants in the room may be exposed to a potential health hazard without the occupants having any warning or knowledge of the risk.

According to some example embodiments, there is provided a safety system that is configured to check suitability of a cartridge placed in a device prior to atomizing its contents. In some example embodiments, the safety system may also be configured to monitor expiration date of the cartridge being used and may provide warning when contamination or tampering is suspected. Optionally, the safety system may halt activity of the aerosol dispensing device whenever contamination or tampering is suspected. According to some example embodiments, a cartridge that is configured to be used with the device is installed with a barcode, e.g. a one dimensional or two dimensional barcode, radio frequency identification (RFID) tag or other electronic identification tag including information that may be recognized by the safety system of the device. Information provided by the tag or code may include one or more of: state of a seal on the cartridge, identification data, part number of the product, batch number, production date, expiration date, quantity of material in the cartridge, contents of the cartridge and operating instructions. Optionally, some of the information may be retrieved from memory in association with an identity code stored in the tag. In some example embodiments, the electronic identification tag may be an active tag that may alter its memory content based on communication with the safety system. Optionally, memory in an active tag may store indication that the dispenser has previously been installed and used in a device, e.g. a same or different aerosol dispersing device and is no longer valid for use. Such indication can prevent use of a cartridge that has been refilled with unknown contents.

According to some example embodiments, the safety system includes a reader that is configured to read and optionally communicate with a tag or code on a cartridge. Reading may be based on wireless communication, contactless communication or based on physical contact between the reader and an electronic tag. Optionally, memory associated with the safety system includes information for identifying valid identification codes, e.g. a list of valid identification codes. Optionally, the memory may additionally include a history of cartridges that have been previously installed in the device or optionally in other devices and are therefore invalid. The memory may be memory stored in the device, may be memory stored in a remote server or may be memory in a cloud.

In some example embodiments, the safety system is configured to prevent atomization of the material from a cartridge that has not been authenticated by the safety system. In some example embodiments, the safety system may monitor lapsed time since installment of a cartridge and may initiate an alert and stop actuation of the atomization based on detecting that an expiration date of the cartridge has been exceeded. Optionally, the alert may be transmitted to a remote server configured to monitor operation a plurality of aerosol dispersion devices.

According to some example embodiments, the aerosol dispensing device additionally includes a regulator configured to regulate activity of the device based on input from one or more sensors, e.g. humidity sensors, temperature sensors and level sensors. The one or more sensors may be included in the dispensing device or may be stand alone sensors that transmit data to the dispensing device from a distance. In some example embodiments, an air quality probe similar to E4000 indoor air quality probe offered by NanoSense, France provides input to the dispensing device. Optionally, the regulator is configured to adjust operation of the dispensing device based on input from the one or more sensors. Adjusting the operation may include adjusting frequency and duration for creating aerosol. In some example embodiments, adjusting the operation based on sensor inputs may improve effectiveness of the dispensing device in improving the indoor environment.

The adjustments may be performed automatically and in real time by the regulator without the need for user input. In some example embodiments, the regulator may be configured to initiate the adjustments based on gradual changes in the indoor environment that are sensed by the sensors. In additional embodiments, the regulator is also configured to imitate adjustments due to rapid changes in the indoor environment that are sensed by the sensors. For example, it is known that a rate of growth of pathogens may increase with an increase in temperature and humidity levels. Such changes may be gradual. The regulator may track temperature and humidity levels and may alter a frequency and duration for releasing the aerosol in real time based on the detected temperature and humidity levels. For example, a pro-biotic may be dispersed more frequently when temperature is warmer and more humid. Rapid changes may also occur, for example a level of pollution may change due to a change in a number of occupants in the room or due to pollution brought in by one or more occupants. In some example embodiments, the regulator is configured to respond to rapid changes in the indoor environment in real time by adjusting frequency and duration of dispersion.

Reference is now made to FIGS. 1A and 1B showing a simplified schematic drawing of an example aerosol dispensing device and an example replaceable cartridge respectively and to FIG. 2 showing an example replaceable cartridge installed in an example aerosol dispensing device all in accordance with some example embodiments. An aerosol dispensing device 100 includes a housing 101 that may house an actuator 109 configured to actuate atomization of a liquid 159 in a cartridge 150, an outlet channel 129 from which atomized liquid 125 may be expelled and a circuit 105 configured to control operation of actuator 109. An atomizer for creating aerosol 125 based on actuation with actuator 109, may be integrated as part of actuator 109 or may be integrated in cartridge 150. Optionally, actuator 109 is configured to establish fluid connection with cartridge 150. According to some example embodiments, aerosol dispensing device 100 additionally includes a reader 106 configured to read data on a tag 160 included on cartridge 150.

In some example embodiments, device 100 is self-powered with a power source 108. Alternatively, device 100 may be powered by an external power source. In some example embodiments, device 100 includes a user interface including for example a display 103 and one or more user actuated buttons or knobs 107. Optionally, device 100 additionally includes a sensor 117 configured to sense when cartridge 150 is installed in device 100. Sensor 117 may for example be an opto-coupler sensor that detects a break in a line of sight due to insertion of neck 152 into actuator 109. In another example, sensor 117 may be a button switch that is compressed based on insertion of collar 152 into actuator 109.

Device 100 may be positioned in an indoor environment. The indoor environment may be a public space such as a hospital or a shopping center or may be a personal space such as an office, a home or a vehicle. Optionally, device 100 may be configured to direct aerosol 125 expelled from channel 129 into airflow ducts of a heating, ventilation and air conditioning (HVAC) system. Optionally, circuit 105 is in communication or receives input from an HVAC system and is operated in coordination with the HVAC system. Alternatively, device 100 may be operated independently from an HVAC system and the aerosol may also be dispersed directly into the indoor space, e.g. not through the HVAC ducts.

According to some example embodiments, liquid 159 may include sensitive material such as a pro-biotic, medicament, nutraceutical, or combinations thereof that may be prone to contamination. The material when contaminated may pose a health hazard. Furthermore, any malicious tampering with cartridge 150 may also lead to a hazardous situation. For example an offender may maliciously insert a harmful bacteria or an irritant into cartridge 150. Alternately, an offender may attempt to refill cartridge 150 with unknown or unregulated contents that may not be suitable or safe in general or for a particular indoor space. In other examples, a hazardous situation may be created without malicious intent, for example when a solution in the cartridge has passed its expiration date or when a property of the solution has been altered due to prolonged exposure to humidity or air.

According to some example embodiments, circuit 105 includes safety verification functionality to verify compatibility, authenticity and safety of cartridge 150 when it is inserted into housing 101 and optionally to provide ongoing monitoring while cartridge 150 is maintained in device 100. The verification may be based on input received from reader 106. In some example embodiments, circuit 105 receives data from reader 106 and compares the data received to information stored in memory. Optionally, if an identification code read by reader 106 matches an identification code listed in the memory, verification may be established. The memory may be memory included in circuit 105, memory included in a remote server 800 or memory included in a cloud. Optionally, the information needed to verify authentication of cartridges may be uploaded by a remote server 800 and circuit 105 may access the information based on wireless communication. According to some example embodiments, circuit 105 is configured to terminate dispersion or formation of atomized liquid 125 and provide an alert when cartridge 150 cannot be positively verified.

Reader 106 may be configured to scan a code or interrogate a tag 160 positioned on cartridge 150, when cartridge 150 is installed in device 100 and provide the data to circuit 105. In some examples, reader 106 is or includes a camera or a RFID scanner that is configured to detect data stored on cartridge 150. Preferably, reader 106 is an active reader that is controlled and powered with circuit 105. In some example embodiments, controller 105 activates reader 106 at a defined frequency, e.g. every 5-60 minutes to scan or interrogate tag 160. Additionally or alternatively, controller 105 may activate reader at defined events. For example controller 105 may activate reader when power of device 100 is turned on and during installation of cartridge 150 in the device 100. In some example embodiments communication between reader 106 and tag 160 is wireless or contactless. In other example embodiments, communication between reader 106 and tag 160 is based on electrical contact.

Optionally, cartridge 150 configured for use with device 100 includes tag or code 160 with data to verify its compatibility. Tag or code 160 may be a barcode, e.g. a one dimensional or two dimensional barcode, may be in passive RFID tag and may be an active RFID tag. Tag or code 160 may be positioned in an inner surface of cartridge 150 that is in contact with fluid 159 or may be positioned on an outer surface of cartridge 150. According to some example embodiments, tag or code 160 may be positioned on cartridge 150 so that it aligns with reader 106 while establishing a sealed connection with actuator 109.

In some example embodiments, tag or code 160 includes passive storage. Information tagged or coded on tag or code 160 may include one or more of the following items: state of a seal on the cartridge, identification data, part number of the product, batch number, production date, expiration date, quantity of material in the cartridge, contents of the cartridge and operating instructions.

Optionally, contents 159 of cartridge 150 are sealed with a seal under cap 151 that is configured to be broken in actuator 109 while inserting cartridge 150 into housing 101. Optionally, breaking of the seal alters data stored in tag or code 160 so that the event may be recorded and detected by reader 106. Optionally, this information may be used to prevent operating device 100 with cartridges that have been refilled. Cartridge 150 may be in the form of a bottle or may be any container that can contain fluid 159 to be dispersed as an aerosol. Typically cartridge 150 is configured to be replaced after its contents have been emptied.

In some example embodiments, tag 160 may be an active tag and reader 106 may transmit data to tag 160 that may be stored in tag 160. Active storage may be a microchip with RAM memory in which case a small power source may be included on cartridge 150. Alternatively, active storage may be an active RFID.

Figure 1A:
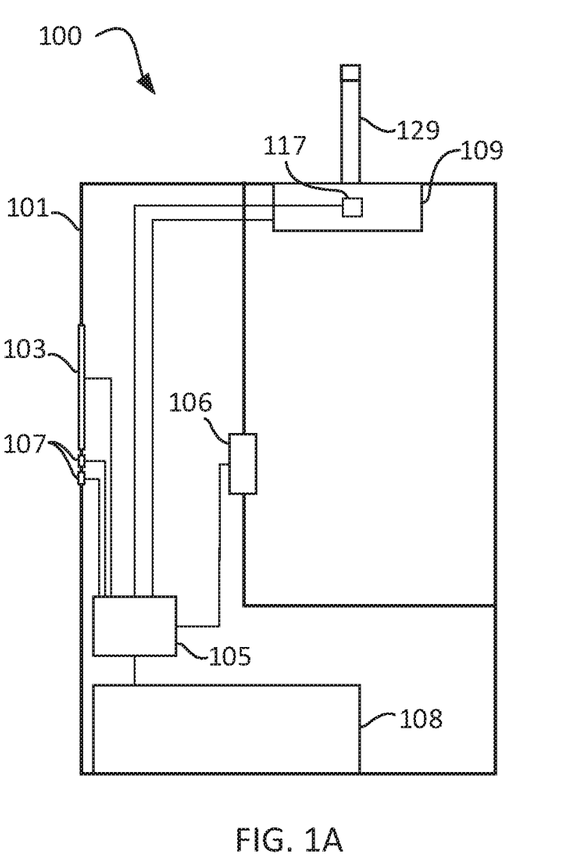
FIGS. 1A and 1B are simplified schematic drawing of an example aerosol dispensing device and an example replaceable cartridge respectively in accordance with some example embodiments.
Figure 1B:
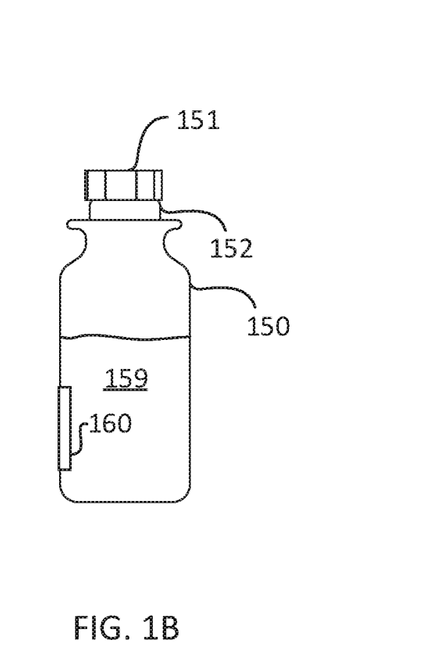
Figure 2:
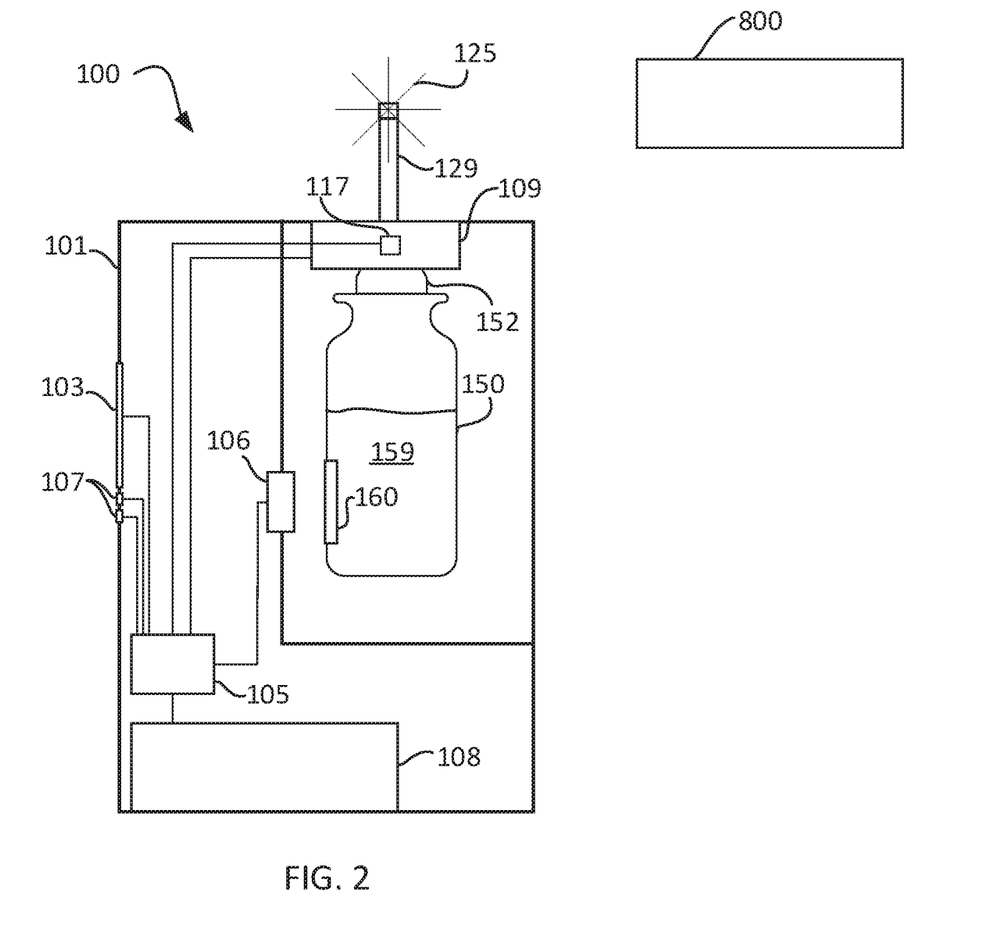
FIG. 2 is a simplified schematic drawing of an example replaceable cartridge installed in an example aerosol dispensing device in accordance with some example embodiments.
Figure 3:
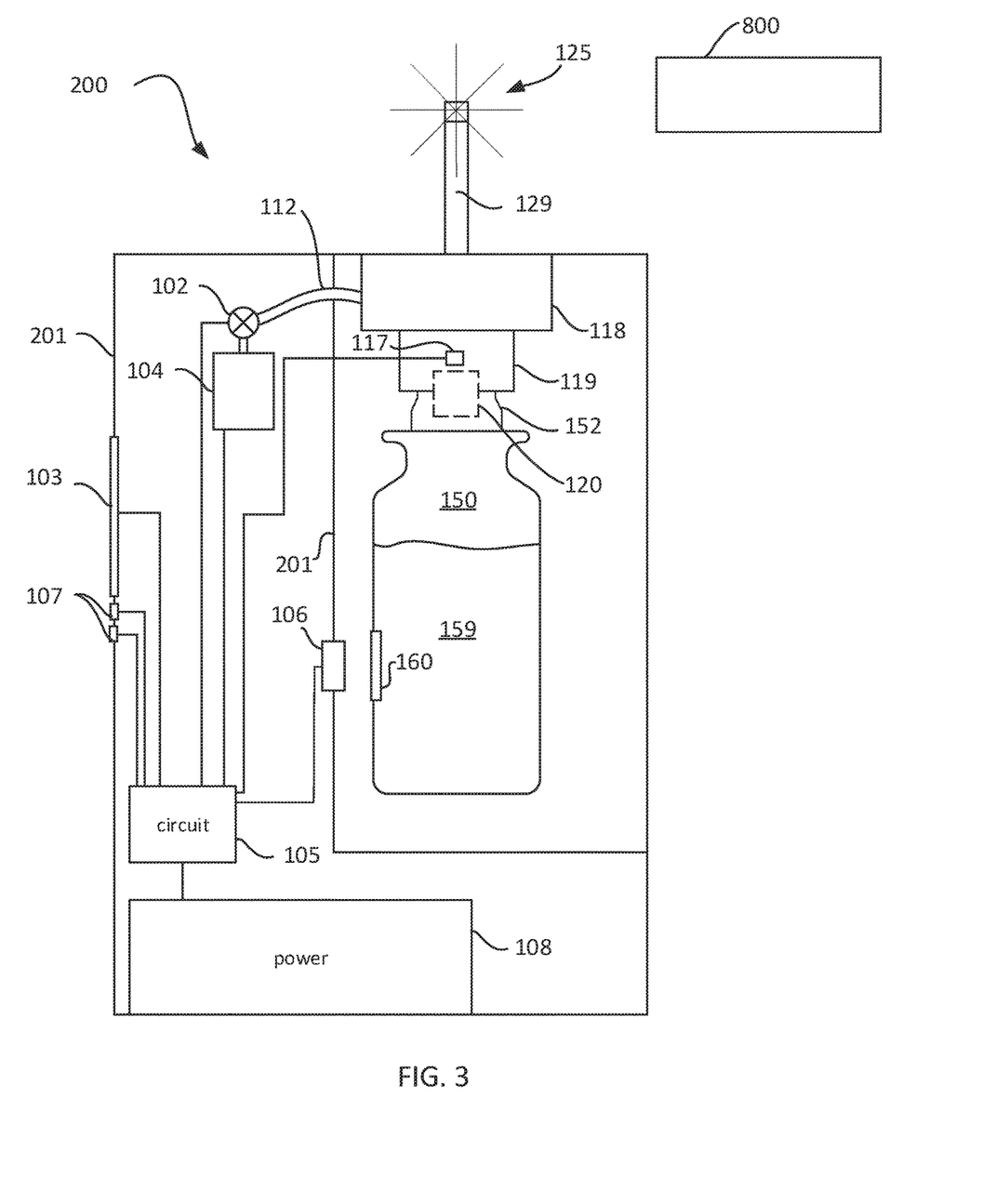
FIG. 3 shows a simplified schematic drawing of an example aerosol dispensing device with a replaceable cartridge that is actuated with compressed air in accordance with some example embodiments.

Reference is now made to FIG. 3 showing a simplified schematic drawing of an example aerosol dispensing device with a replaceable cartridge that is actuated with compressed air in accordance with some example embodiments. An aerosol dispensing device 200 includes a housing 201 that may house an air compressor 104 to actuate atomizing a liquid 159 contained in a cartridge 150. Pressurized air provided by compressor 104 may be delivered through valve 102 and a channel 112, e.g. a tube to a connector 118. Connector 118 may establish a fluid connection between compressor 104, cartridge 150 and an aerosol outlet 129. An atomizer 120 may be integrated in connector 118 or in collar 152 of cartridge 150. Optionally, an adaptor 119 provides a sealed connection between cartridge 150 and connector 118. Although connector 118 and adaptor 119 are shown as two separate elements, it is understood that functionality of these two elements may be integrated into a single part.

In some example embodiments, circuit 105 verifies and monitors that cartridge 150 is safe to use based on input from reader 106 included in device 200. As long as the input received indicates that cartridge 150 is safe for use, controller 105 may authorize actuation of valve 102. In some example embodiments, whenever, input from reader 106 indicates that cartridge 150 is not safe for use, controller 105 may interrupt operation of valve 102 to prevent dispersion 125 of material from cartridge 150 until safety is affirmed. Optionally, controller 105 may also provide a warning, e.g. an audio warning, a warning displayed on display 103 or a warning transmitted to a remote server 800. A determination that cartridge 150 is not safe for use may be based on circuit 105 determining that the identity of the cartridge cannot be verified, that the expiration date has been exceeded or that the cartridge has been tampered with.

Figure 4:
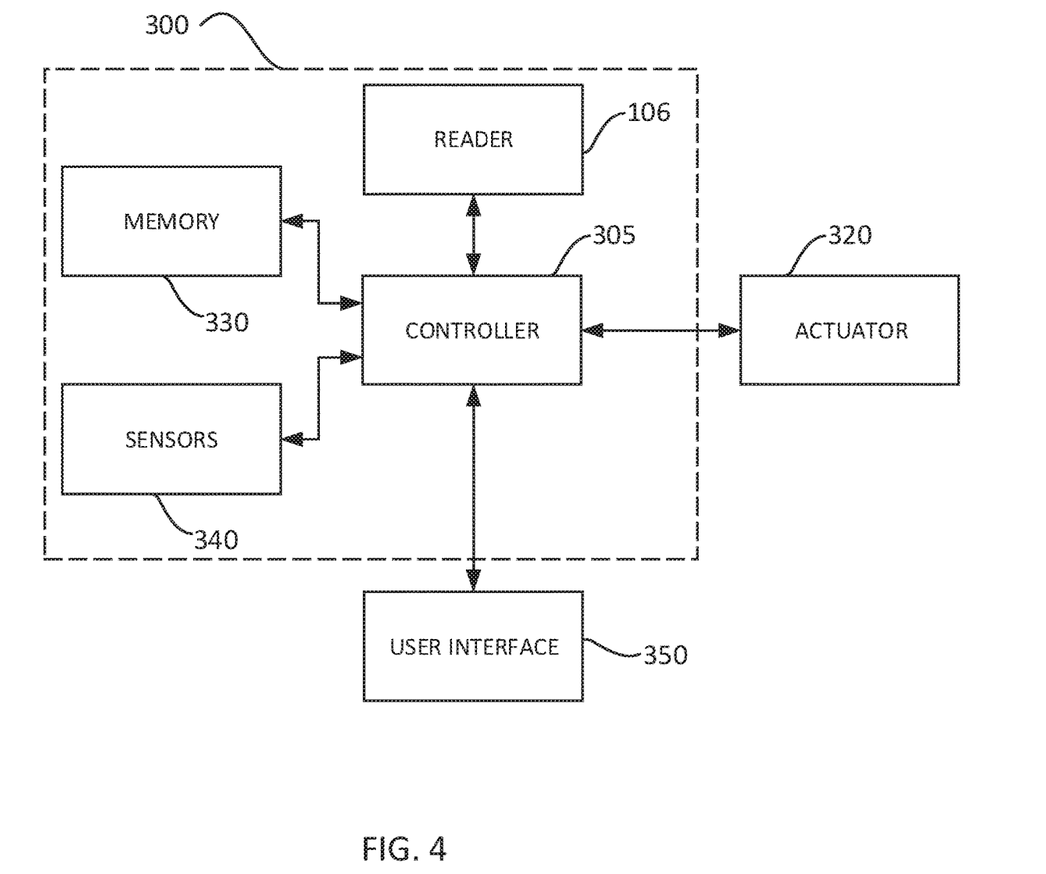
FIG. 4 is a simplified block diagram of an example safety system for an aerosol dispensing device in accordance with some example embodiments.

FIG. 4 shows a simplified block diagram of an example safety system for an aerosol dispensing device in accordance with some example embodiments. According to some example embodiments, a safety system 300 includes a reader 106 configured to scan or interrogate a tag 160 on cartridge 150, memory 330 including information for verifying authenticity and compatibility of cartridge 150 and a controller 305 configured to perform the verification and to selectively activate an actuator that forms the aerosol based on the verification made. Optionally, safety system 300 includes one or more sensors 340, e.g. a sensor configured to detect breaking of a seal on cartridge 150. Controller 305 may receive input from sensors 340 and use the input to verify authenticity of cartridge 150. Controller 305, e.g. functionality of controller 305 may be incorporated into circuit 105.

Controller 305 may retrieve information from memory 330 and identify compatibility based on comparing data read from reader 310 with data stored in memory 330. Optionally, memory 330 includes pre-defined data such as a list of valid identification numbers that may be used by controller 305 to identify cartridge 150. Memory 330 may also be configured to store data read from a cartridge 150, e.g. expiration date, contents and preferable parameters of operation with the cartridge. Memory 330 may be memory included in circuit 105 or may be remote memory, e.g. memory in a cloud that may be accessed by controller 305 based on wireless communication.

In some example embodiments, when controller 305 identifies a lack of compatibility, an alert may be provided to a user interface 350 and optionally a remote server 800. User interface 350 may for example include a display 103 or a microphone via which an audio alert is provided. Optionally, a user may initiate a compatibility and safety check via user interface 350, e.g. via user actuated buttons 107 and display 103.

Figure 5:
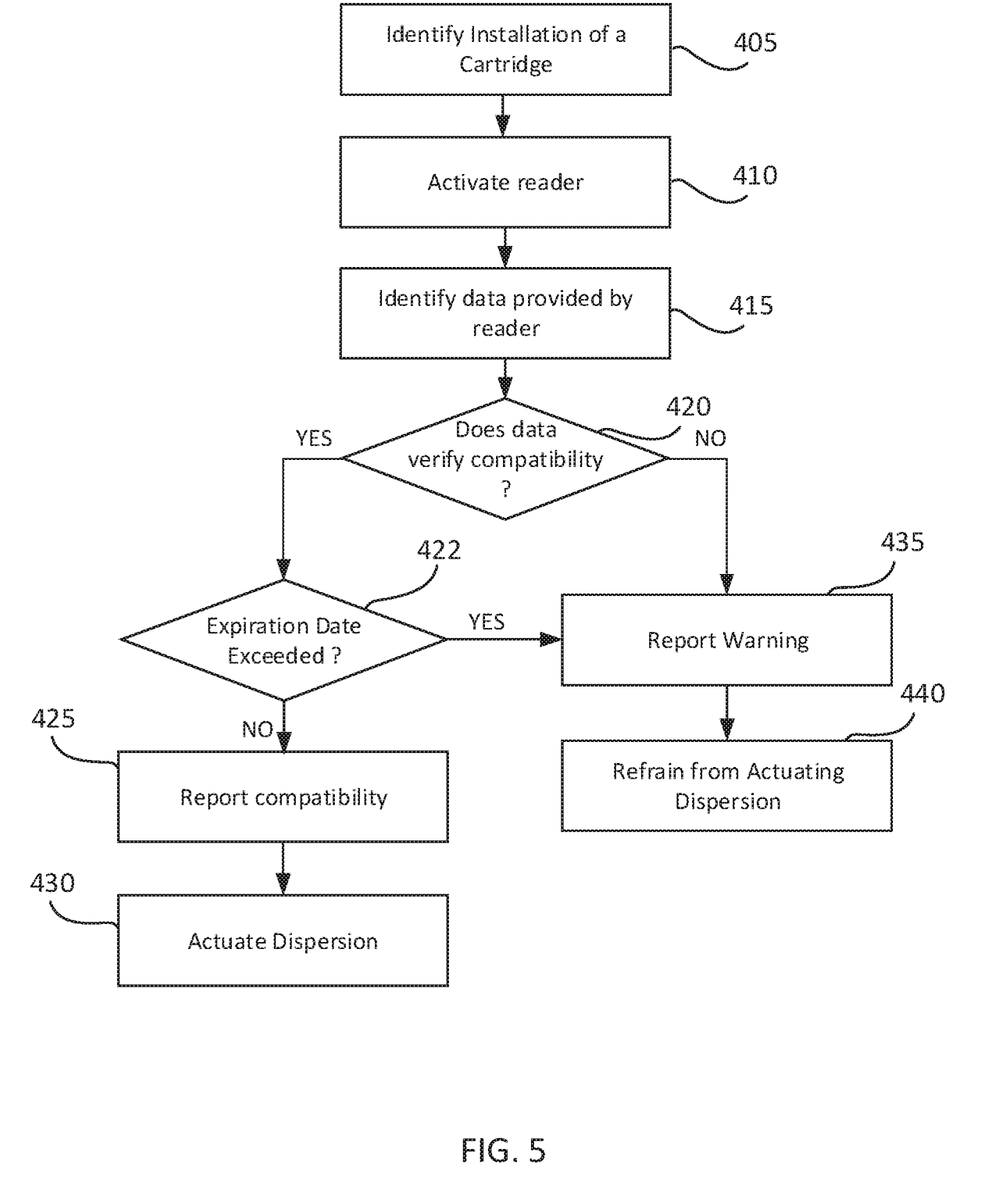
FIG. 5 is a simplified flow chart of an example method for monitoring authenticity and safety of a cartridge installed in the aerosol dispensing device in accordance with some example embodiments.

FIG. 5 shows a simplified flow chart of an example method for monitoring authenticity and safety of a cartridge installed in the aerosol dispensing device in accordance with some example embodiments. In some example embodiments, a controller of a safety system may detect that a new cartridge has been installed in an aerosol dispensing device (block 405) and activate a reader to verify authenticity and/or compatibility of the cartridge (block 410). Detection may be based on input from a sensor, e.g. sensor 117 or may be based on detecting a change in data read by the reader in response to periodic interrogation by the reader. Input from the reader may be identified and optionally compared to data stored in memory (block 415). Compatibility or authenticity of the cartridge may be verified (block 420). If the verification is positive, an expiration date of the cartridge may be checked (block 422). If the expiration date has been exceeded, an error may be reported (block 435) and the controller may halt operation of the actuator configured for actuating the atomization (block 440). If the expiration date has not been exceeded, compatibility may be reported to a user interface (block 425) and dispersion of material included in the cartridge may be actuated. If the verification is negative, an error may be reported (block 435) and the controller may halt operation of the actuator configured for actuating the dispersion (block 440).

Figure 6:
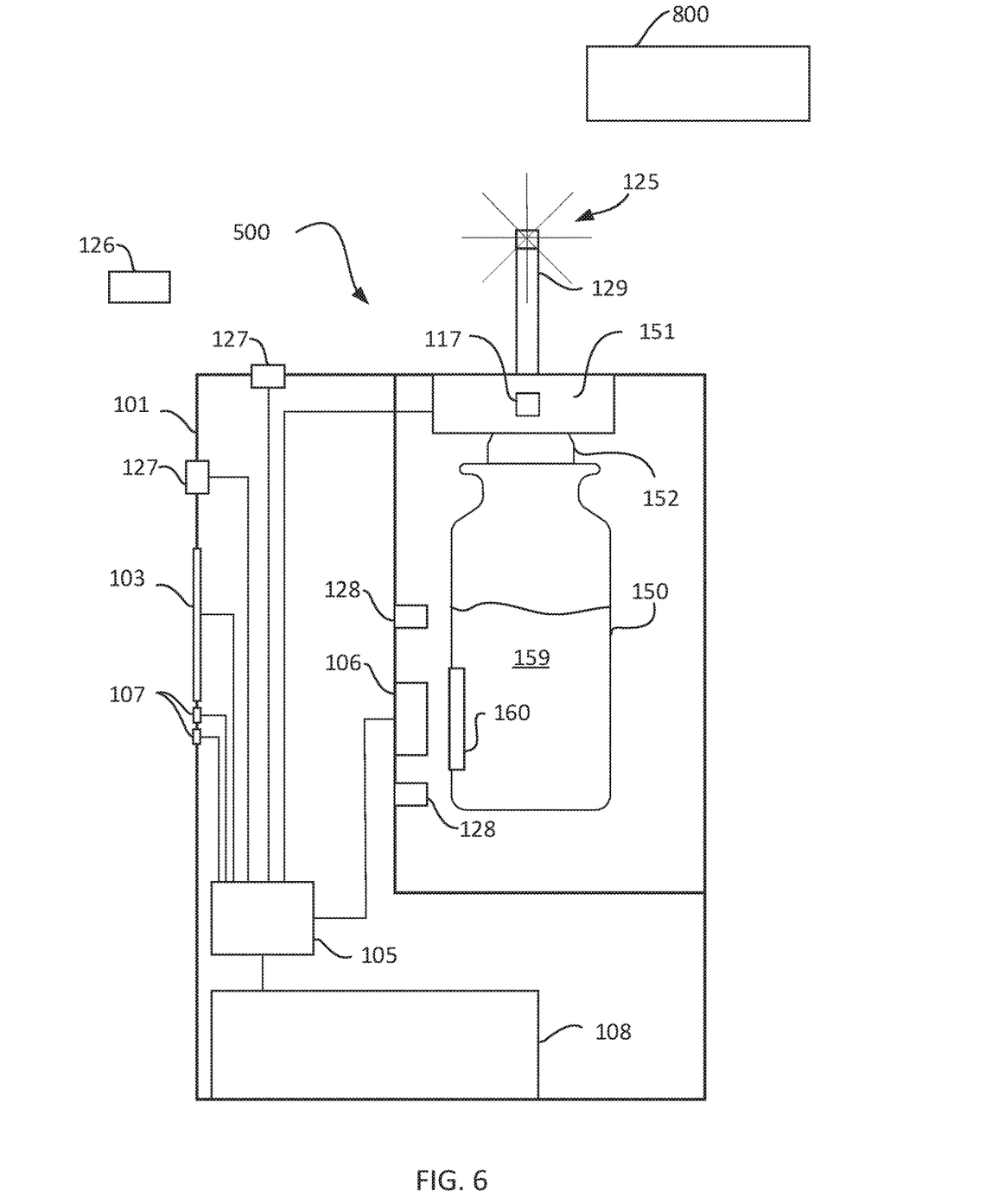
FIG. 6 is simplified schematic drawing of an example aerosol dispensing device including one or more sensors in accordance with some example embodiments.

FIG. 6 shows a simplified schematic drawing of an example aerosol dispensing device including one or more sensors in accordance with some example embodiments. According to some example embodiments, the aerosol dispensing device 500 includes a regulator configured to regulate activity of device 500 installed with a cartridge 150. Functionality of the regulator may be included in circuit 105. Optionally, device 500 includes reader 106 and circuit 105 may regulate activity of device 500 based on information received from reader 106, e.g. instruction that may be specific to liquid 159 contained in the cartridge. Circuit 105 may additionally or alternatively regulate activity of device 500 based on inputs from one or more sensors in communication with circuit 105. In some example embodiment, device 500 includes sensors 128 configured to detect a parameter related to content 159 in cartridge 150. Optionally, sensor 128 is a level sensor for detecting a level of liquid 159 in cartridge 150. Optionally, one sensor 128 may be positioned to sense liquid at 1-3 cm from a bottom of cartridge 150 to detect when contents of cartridge 150 are nearly emptied. In some example embodiments, when contents of cartridge 150 are nearly emptied, circuit 105 may provide an alert on display 103 and may also communicate this information to a remote server 800 in communication with circuit 105. Remote server 800 may then alert a service provider or deliver a new cartridge to the site including device 500.

Device 500 may additionally include sensors 127 that may detect environmental conditions. Optionally, humidity is detected. In some example embodiments, temperature is detected. At times, an expiration date may be adjusted based on the detected environmental conditions. For example an expiration date may be shortened in environments with higher humidity as compared to environments that are more arid. Optionally, frequency or duration of actuation may be adjusted based on output detected from one or more of sensors 127, sensors 128 and based on data read with reader 106.

In some example embodiments, device 500 may be configured to receive input from a stand-alone sensor 126 that is remote from device 500. Input may be received based on tethered or wireless connection. Stand-alone sensor 126 may be for example an air quality probe similar to E4000 indoor air quality probe offered by NanoSense, France, a thermostat associated with an HVAC, or a humidity sensor. Input from remote sensors 126 may similarly be used to adjust an expiration date or to adjust frequency or duration of actuation based on the detected environmental conditions.

According to some example embodiments, the aerosol dispensing device 500 additionally includes safety verification functionality as described herein above to verify compatibility, authenticity and safety of cartridge 150 when it is inserted into device 500 and optionally to provide ongoing monitoring while cartridge 150 is maintained in device 500. In some example embodiments, the safety verification functionality is based on reader 106 reading data on a tag 160 included on cartridge 150 and circuit 105 processing the data.

Figure 7:
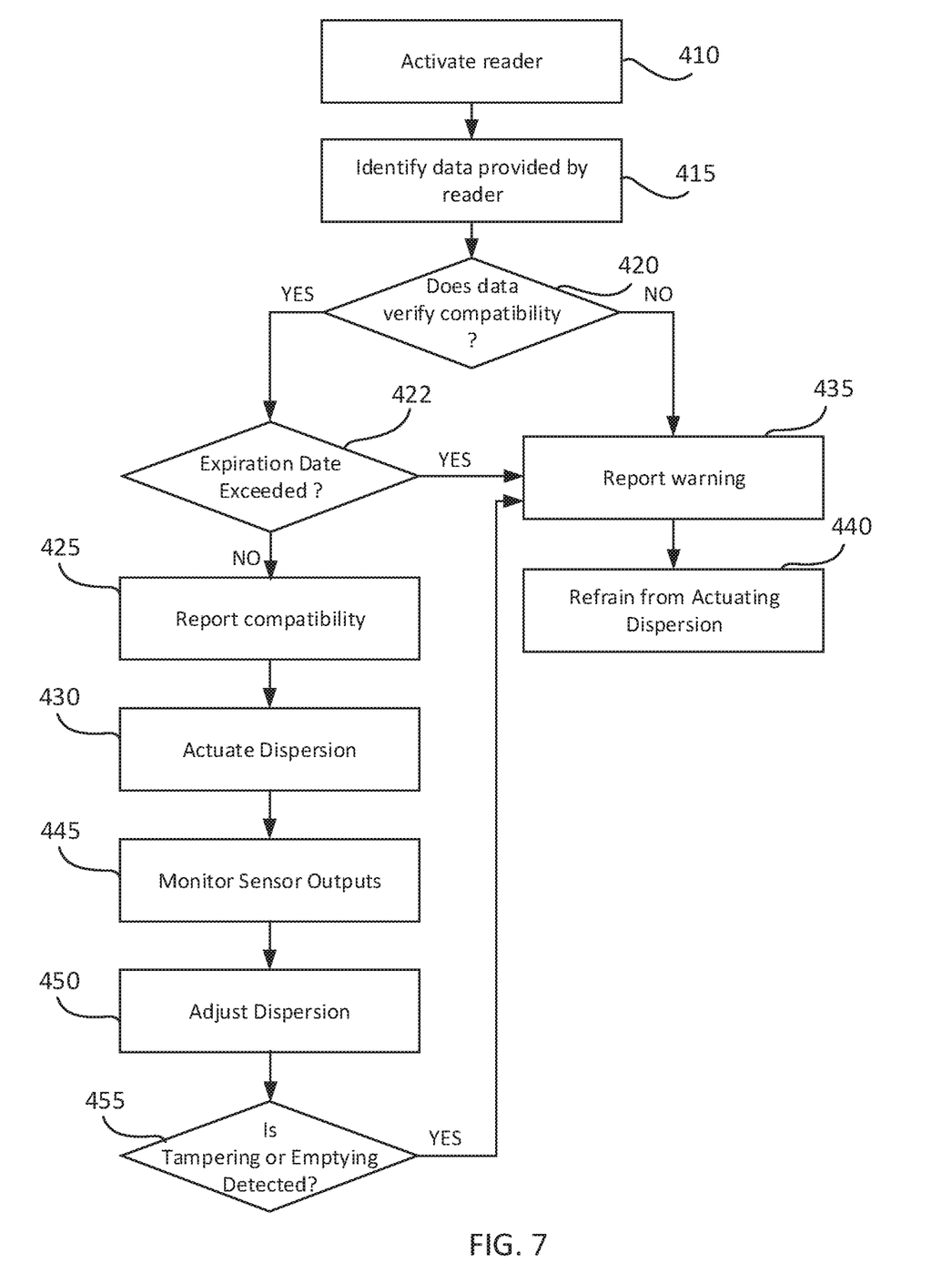
FIG. 7 is a simplified flow chart of an example method for operating an aerosol dispensing device in accordance with some example embodiments.

FIG. 7 shows a simplified flow chart of an example method for operating an aerosol dispensing device in accordance with some example embodiments. The method in FIG. 7 is similar to the method of FIG. 5 with some additional steps. In some example embodiments, in addition to verifying compatibility of a cartridge, outputs from one or more sensors are monitored to assess conditions in the surrounding environment (block 445). Activation parameters of the device may be adjusted based on the outputs sensed from the sensors (block 450). Parameters that may be adjusted include for example, frequency of atomization, duration of the atomization and quantity of atomized liquid. In some example embodiments, output from the sensor may also indicate tampering (block 455). When tampering is detected, an error warning may be provided (block 435) and the safety system may block actuation of the dispersion (block 440) Likewise when emptying of the cartridge is detected an error warning may be provided (block 435) and the safety system may block actuation of the dispersion (block 440).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements. In addition, any priority document(s) of this application is/are hereby incorporated herein by reference in its/their entirety.

What is claimed is:

1. An aerosol dispensing device for restoring biological balance in a space, the aesosol dispensing device comprising:
   an atomizer configured to atomize a liquid contained in a cartridge, the liquid containing biological content, the biological content being one member of the group consisting of microorganisms, a pro-biotic, a medicament, and a nutraceutical;
   an actuator configured to actuate activity of the atomizer at a defined frequency and for a defined duration, wherein the actuation is performed automatically without human intervention;
   a controller configured to:
      to receive input from a first sensor configured to sense a parameter related to an indoor environment around the aerosol dispending device, the parameter relating to air quality in the space; and
      to adjust at least one of the defined frequency and the defined duration based on the input received, wherein the adjusting is performed automatically without human intervention, to spread said bological content around said space in response to said sensed parameter, thereby to restore said biological balance in said space.

2. The device of claim 1, wherein the first sensor is selected from a group including: a temperature sensor, a humidity sensor, and an air quality probe.

3. The device of claim 1, wherein the controller is configured to receive the input from the first sensor via a wireless communication channel.

4. The device of claim 1 wherein the first sensor is included in the device.

5. The device of claim 1 comprising a second sensor configured for sensing a second parameter related to the liquid.

6. The device of claim 5, wherein the second parameter is a level of the liquid.

7. The device according to claim 1 comprising:
   a reader configured to read data attached to the cartridge while the cartridge is installed in the device; wherein the controller is further configured to:

receive data from the reader;

verify authenticity of the cartridge based on the data received;

initiate activity of the actuator based on verifying that the cartridge is authentic; and block activity of the actuator based on verifying that the cartridge is not authentic.

8. The device of claim 7, wherein the controller is configured to compare the data from the reader with reference data stored in memory and to verify authenticity based on the comparison wherein the memory is in a cloud and wherein the controller is configured to receive the reference data based on wireless communication or wherein the memory is in a remote server that is configured to monitor operation of a plurality of aerosol dispensing devices.

9. The device of claim 7, wherein the data attached to the cartridge is in the form of an active electronic tag and wherein the reader is configured alter data stored in the active electronic tag.

10. The device of claim 7, comprising a user interface and wherein the controller is configured to provide an alert to at least one of the user interface based on verifying that the cartridge is not authentic and a remote server based on verifying that the cartridge is not authentic.

11. The device of claim 7, wherein the controller is configured to monitor ongoing use of the cartridge and to block activity of the actuator based on determining a change in safety of the cartridge and wherein the change is due to one or more of detecting that an expiration date of the cartridge has passed and the liquid in the cartridge has been emptied.

12. The device of claim 7, wherein the data from the reader includes one or more of: state of a seal on the cartridge, identification data, part number of the product, batch number, production date, expiration date, quantity of material in the cartridge, contents of the cartridge and operating instructions.

13. The device of claim 7, comprising a third sensor configured to sense installation of the cartridge in the device and wherein the controller is configured to initiate reading the data attached to the cartridge based on the controller identifying that the cartridge has been installed.

14. The device of claim 1, wherein the controller is configured to receive input from an HVAC system and to coordinate activity of the actuator based on the input received from the HVAC.

15. A method for selectively altering microorganism balance in an indoor environment comprising:

providing an aerosol dispensing device comprising:

a liquid contained in a cartridge, the cartridge containing biological content, said biological content being one member of the group consisting of microorganisms, a pro-biotic, a medicament, and a nutraceutical probiotic content;

an atomizer configured to atomize the liquid contained in the cartridge; and an actuator configured to actuate activity of the atomizer at a defined frequency and for a defined duration, wherein the actuation is performed automatically without human intervention;

actuating activity of the atomizer at a defined frequency and for a defined duration;

receiving input from a first sensor configured to sense a parameter related to air quality of an indoor environment around the aerosol dispending device; and adjusting at least one of the defined frequency and the defined duration based on the input received to spread said biological content around said indoor environment in response to said parameter related to air quality, wherein the adjusting is performed automatically without human intervention, in order to selectively alter said microorganism balance in said indoor environment.

16. The method of claim 15, wherein the first sensor is selected from a group including: a temperature sensor, a humidity sensor and an air quality probe.

17. The method of claim 15, wherein the input from the first sensor is received via a wireless communication channel.

18. The method of claim 15 wherein a second sensor senses a second parameter related to the liquid and adjusting at least one of frequency and duration of activity of the actuator based on the second parameter.

19. The method of claim 18, wherein the second parameter is a level of the liquid in the cartridge.

20. The method of claim 15 comprising:

providing an aerosol dispensing device comprising:

a reader configured to read data attached to the cartridge while the cartridge is installed in the device;

receiving data from the reader;

verifying authenticity of the cartridge based on the data received;

initiating activity of the actuator based on verifying that the cartridge is authentic; and blocking activity of the actuator based on verifying that the cartridge is not authentic.

21. The method of claim 20, comprising comparing the data from the reader with reference data stored in memory; wherein the verifying is also based on the comparing, wherein the memory is in a cloud and wherein the reference data is received based on wireless communication.

22. The method of claim 20, comprising sensing installation of the cartridge with a third sensor in the device and initiating reading the data attached to the cartridge based on identifying that the cartridge has been installed.

23. The method of claim 20, wherein the data attached to the cartridge is in the form of an active electronic tag and wherein the reader is configured alter data stored in the active electronic tag.

24. The method of claim 20, comprising providing an alert to one or more of a user interface of the device and a remote server based on verifying that the cartridge is not authentic.

25. The method of claim 20, comprising monitoring ongoing use of the cartridge and blocking activity of the actuator based on determining a change in safety of the cartridge, wherein detecting the change includes one or more of detecting that an expiration date of the cartridge has passed and the liquid in the cartridge has been emptied.

26. The method of claim 20, wherein the data from the reader includes one or more of: state of a seal on the cartridge, identification data, part number of the product, batch number, production date, expiration date, quantity of material in the cartridge, contents of the cartridge and operating instructions.

27. The method of claim 15, comprising receiving input from an HVAC system and coordinating activity of the actuator based on the input received from the HVAC.

28. An aerosol dispensing device comprising:

an atomizer configured to atomize a liquid contained in a cartridge, the liquid containing biological content;

an actuator configured to actuate activity of the atomizer at a defined frequency and for a defined duration, wherein the actuation is performed automatically without human intervention;

a controller configured to:

receive input from a first sensor configured to sense a first parameter related to an indoor environment around the aerosol dispending device;

receive input from a second sensor configured to obtain a second parameter, said second parameter relating to said biological content;

and adjust at least one of the defined frequency and the defined duration based on the input received, wherein the adjusting is performed automatically without human intervention;

is performed automatically without human intervention.

29. The device of claim 28, wherein the biological content is one member of the group consisting of microorganisms, a pro-biotic, a medicament, and a nutraceutical.

* * * * *